US009095679B2

(12) United States Patent
Nishimura et al.

(10) Patent No.: US 9,095,679 B2
(45) Date of Patent: Aug. 4, 2015

(54) CATHETER ASSEMBLY

(71) Applicant: Terumo Kabushiki Kaisha, Tokyo (JP)

(72) Inventors: Yuka Nishimura, Tsukuba (JP);
Hidenori Tanabe, Yamanashi (JP);
Yasuhiro Ueda, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/227,941

(22) Filed: Mar. 27, 2014

(65) Prior Publication Data
US 2014/0213987 A1 Jul. 31, 2014

Related U.S. Application Data

(63) Continuation of application No. PCT/JP2012/073328, filed on Sep. 12, 2012.

(30) Foreign Application Priority Data

Sep. 28, 2011 (JP) ................. 2011-212694

(51) Int. Cl.
*A61M 5/178* (2006.01)
*A61M 25/00* (2006.01)
*A61M 25/06* (2006.01)
*A61M 39/06* (2006.01)

(52) U.S. Cl.
CPC ....... *A61M 25/0075* (2013.01); *A61M 25/0084* (2013.01); *A61M 25/0606* (2013.01); *A61M 2039/064* (2013.01); *A61M 2039/0653* (2013.01)

(58) Field of Classification Search
CPC ............ A61M 39/26; A61M 25/0097; A61M 25/0017; A61M 2039/1077; A61M 25/0014; A61M 2039/062; A61M 39/0613; A61M 2039/0633; A61M 25/0075; A61M 39/06; A61M 2039/064; A61M 25/0084; A61M 25/0606; A61M 2039/0653; A61B 5/150221; A61B 5/150488; A61B 5/150496; A61B 5/150511; A61B 5/150519; Y10S 128/912
USPC ..................................................... 604/167.01
See application file for complete search history.

(56) References Cited

U.S. PATENT DOCUMENTS

| 5,149,327 | A | 9/1992 | Oshiyama |
| 2009/0281525 | A1 | 11/2009 | Harding et al. |
| 2010/0204648 | A1 | 8/2010 | Stout et al. |
| 2011/0046570 | A1 | 2/2011 | Stout et al. |
| 2012/0184910 | A1* | 7/2012 | Woehr ..................... 604/164.08 |

FOREIGN PATENT DOCUMENTS

JP 07-148265 A 6/1995

OTHER PUBLICATIONS

International Search Report dated Dec. 18, 2012 issued in International Application No. PCT/JP2012/073328.

* cited by examiner

*Primary Examiner* — Jason Flick
(74) *Attorney, Agent, or Firm* — Foley & Lardner LLP

(57) ABSTRACT

A catheter assembly includes a tubular insertion portion; a support portion that is connected to a proximal end side of the insertion portion and has therein a flow passage communicating with an inside of the insertion portion; a valve body that is disposed in the flow passage and includes: a blocking membrane configured to inhibit a flow of fluid, and an opening/closing part configured such that the blocking membrane is at least partially openable and closeable via the opening/closing part; and an insertion member which is arranged proximal of the blocking membrane and is insertable into the opening/closing part by moving in a distal direction. The opening/closing part is formed as a single slit penetrating the blocking membrane, the slit having a distal end opening and a proximal end opening, and a length of the distal end opening being smaller than a length of the proximal end opening.

6 Claims, 8 Drawing Sheets

FIG. 8

| EXAMPLE | COMPARATIVE EXAMPLE 1 | COMPARATIVE EXAMPLE 2 | COMPARATIVE EXAMPLE 3 | COMPARATIVE EXAMPLE 4 |
|---|---|---|---|---|
| Lr=0.4mm<br>Lf=0.3mm | Lr=0.3mm<br>Lf=0.3mm | Lr=0.4mm<br>Lf=0.4mm | Lr=0.3mm<br>Lf=0.4mm | |
| GOOD PENETRABILITY | BAD PENETRABILITY | GOOD PENETRABILITY | BAD PENETRABILITY | GOOD PENETRABILITY |
| GOOD HEMOSTATIC | GOOD HEMOSTATIC | BAD HEMOSTATIC | GOOD HEMOSTATIC | BAD HEMOSTATIC |

CATHETER ASSEMBLY

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/073328 filed on Sep. 12, 2012, which is based upon and claims the benefit of priority of Japanese Application No. 2011-212694 filed on Sep. 28, 2011, the entire contents of which are hereby incorporated by reference in their entireties.

BACKGROUND

1. Technical Field

The present disclosure relates to a catheter assembly which dwells in a blood vessel or on a skin of a patient, allowing transfusion to the patient.

2. Background Art

Generally, when transfusion is carried out to a patient, an indwelling needle is pierced (inserted) in a blood vessel of a patient so as to dwell in the blood vessel. The distal end portion of a transfusion tube and the proximal end portion of the indwelling needle exposed on the skin are connected to provide communication with the transfusion tube. Therefore, the indwelling needle is configured as a catheter assembly such that the connection with the transfusion tube can rapidly be carried out and the connected portion can easily be allowed to dwell on the skin of the patient (see, e.g., the specification of US 2010/0204648 A).

The catheter assembly disclosed in US 2010/0204648 A includes a catheter, a catheter hub which is connected to the proximal end portion of the catheter, a needle having a sharp needle tip on the distal end, and a needle hub which is connected to the proximal end portion of the needle. Further, in the inside of the catheter hub, a valve mechanism is provided, the valve mechanism being configured with a hemostasis valve which prevents outflow of blood and a plug (pusher) which penetrates a slit of the hemostasis valve.

When using the catheter assembly, the catheter and the needle are integrally pierced in the blood vessel, and then the needle is solely pulled out so as to allow the catheter to dwell in the blood vessel. In this state, the blood flows into a passage in the catheter hub in the proximal end side via the catheter. However, the hemostasis valve contained in the catheter hub prevents the outflow of the blood. Then, the plug is inserted in an opening/closing part of the hemostasis valve and the transfusion tube is connected to the proximal end side of the catheter hub, thereby allowing the transfusion line to communicate with the blood vessel of the patient.

As for the valve mechanism of the catheter assembly, as described above, it is desirable to precisely stop the blood flowing in via the catheter, as well as to allow the connection of the catheter assembly and the transfusion tube to be carried out easily and surely. That is, it is required to simultaneously satisfy both hemostasis of blood and penetrability of the plug when inserted in the hemostasis valve (including easiness, rapidity, or reliability).

However, in the valve mechanism configured with the hemostasis valve and the plug, when hemostasis is to be improved, the slit of the hemostasis valve is configured not to open easily, which reduces penetrability and makes it difficult to insert the plug. On the other hand, when penetrability is to be improved, the opening/closing part of the hemostasis valve is configured to open easily so as to allow the plug to be inserted easily, reducing hemostasis. That is, it is difficult to simultaneously satisfy both hemostasis and penetrability of the valve mechanism of the catheter assembly.

Thus, there is a need for a catheter assembly which can improve hemostasis and penetrability of the valve mechanism using a simple configuration, thereby reducing the outflow of blood from the valve mechanism as well as improving the efficiency of a connecting operation of the transfusion tube.

SUMMARY OF INVENTION

In one embodiment, a catheter assembly includes a tubular insertion portion, a support portion which is connected to the proximal end side of the insertion portion and has therein a flow passage communicating with the inside of the insertion portion, a valve body which is provided in the flow passage and has a blocking membrane stopping the flow of fluid and an opening/closing part allowing the blocking membrane to partially open or close, and an insertion member which is provided closer to the proximal end than the blocking membrane and is inserted in the opening/closing part by moving toward the distal end. The opening/closing part is formed in a single slit shape penetrating the blocking membrane, and is formed to have a relation of $L_f < L_r$, where $L_f$ is a linear length at the distal end opening from which the insertion member protrudes and $L_r$ is a linear length at the proximal end opening in which the insertion member is inserted.

According to this embodiment, the opening/closing part of the hemostasis valve may be formed in a single slit shape penetrating the blocking membrane, and is formed to have the relation of $L_f < L_r$, where $L_f$ is a linear length at the distal end opening from which the insertion member protrudes and $L_r$ is a linear length at the proximal end opening in which the insertion member is inserted. When the insertion member is not inserted in the opening/closing part, the opening/closing part can surely be closed since the linear length $L_f$ at the distal end opening is short, thereby preventing blood from flowing out from the valve body to the proximal end side. When the insertion member is inserted in the opening/closing part, the insertion member can easily enter into the opening/closing part from the proximal end opening since the linear length $L_r$ at the proximal end opening is long. Thus, the hemostasis of blood and the penetrability of the plug are simultaneously improved so that the outflow of blood of the patient can drastically be reduced and further the efficiency of connecting operation of the transfusion tube can be improved.

In one aspect, the opening/closing part is formed in an isosceles trapezoid shape in which the distal end opening and the proximal end opening are the upper base and the lower base of the isosceles trapezoid shape, respectively, in a side cross sectional view of the valve body.

By forming the shape of the opening/closing part in the isosceles trapezoid shape as described above, when inserting the insertion member from the proximal end side of the hemostasis valve, the insertion member inserted from the proximal end opening of the opening/closing part is squeezed by uniform contacting force from both legs of the trapezoid shape and can advance smoothly toward the distal end opening of the opening/closing part, so that the penetrability of the insertion member is further improved.

In one aspect, in the proximal end side of the valve body, a sealing member that is permeable to gas but inhibits permeation of fluid may be arranged so as to block the flow passage.

As described above, by including a sealing member that is permeable to gas but inhibits permeation of fluid, the air existing from the flow passage can be exhausted to the proximal end side, and further, the fluid (blood) which flows into the flow passage can be prevented from flowing out to the proximal end side.

Further, a needle which is inserted in the insertion portion, and a needle hub which is fixed to the proximal end portion of the needle and can be connected to the proximal end side of the support portion may be included.

In this manner, when using the catheter assembly, the insertion portion and the needle can easily be pierced by gripping and operating the needle hub.

According to embodiments of the present invention, by employing a simple configuration, the hemostasis and penetrability of the valve mechanism configured with the valve body and the insertion member can be improved so that the outflow of blood from the valve mechanism is reduced, thereby improving the efficiency of connecting operation of the transfusion tube.

BRIEF DESCRIPTION OF DRAWINGS

FIG. 8 is a table in which penetrability and hemostasis for a slit of a hemostasis valve according to an embodiment and a slit of a hemostasis valve of comparative examples 1 to 4 are shown.

DETAILED DESCRIPTION

A catheter assembly according to embodiments of the present invention will be described in detail below, referring to attached drawings.

Figure 1:
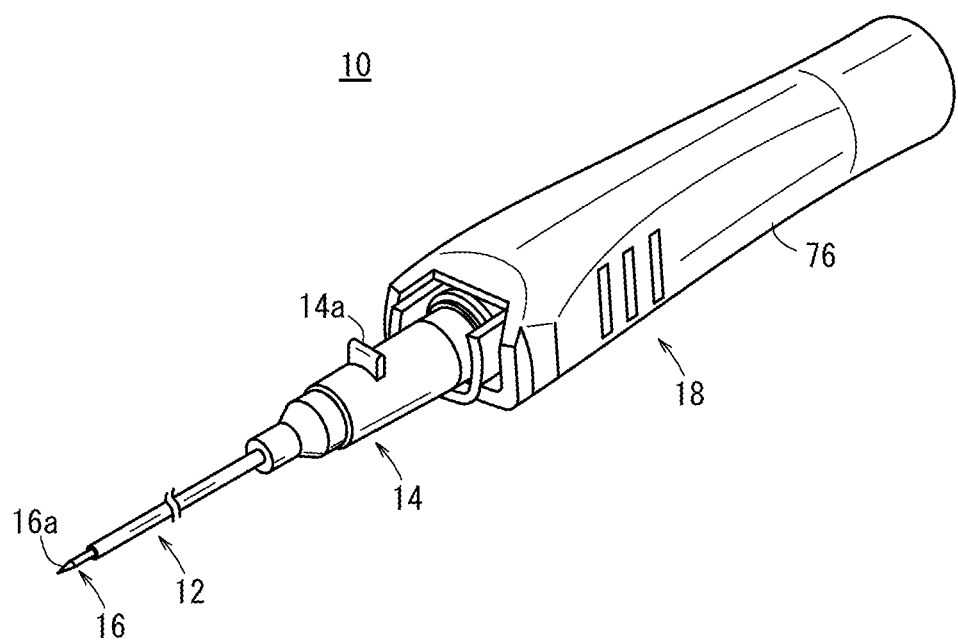
FIG. 1 is an overall perspective view illustrating a catheter assembly according to one embodiment.
Figure 2:
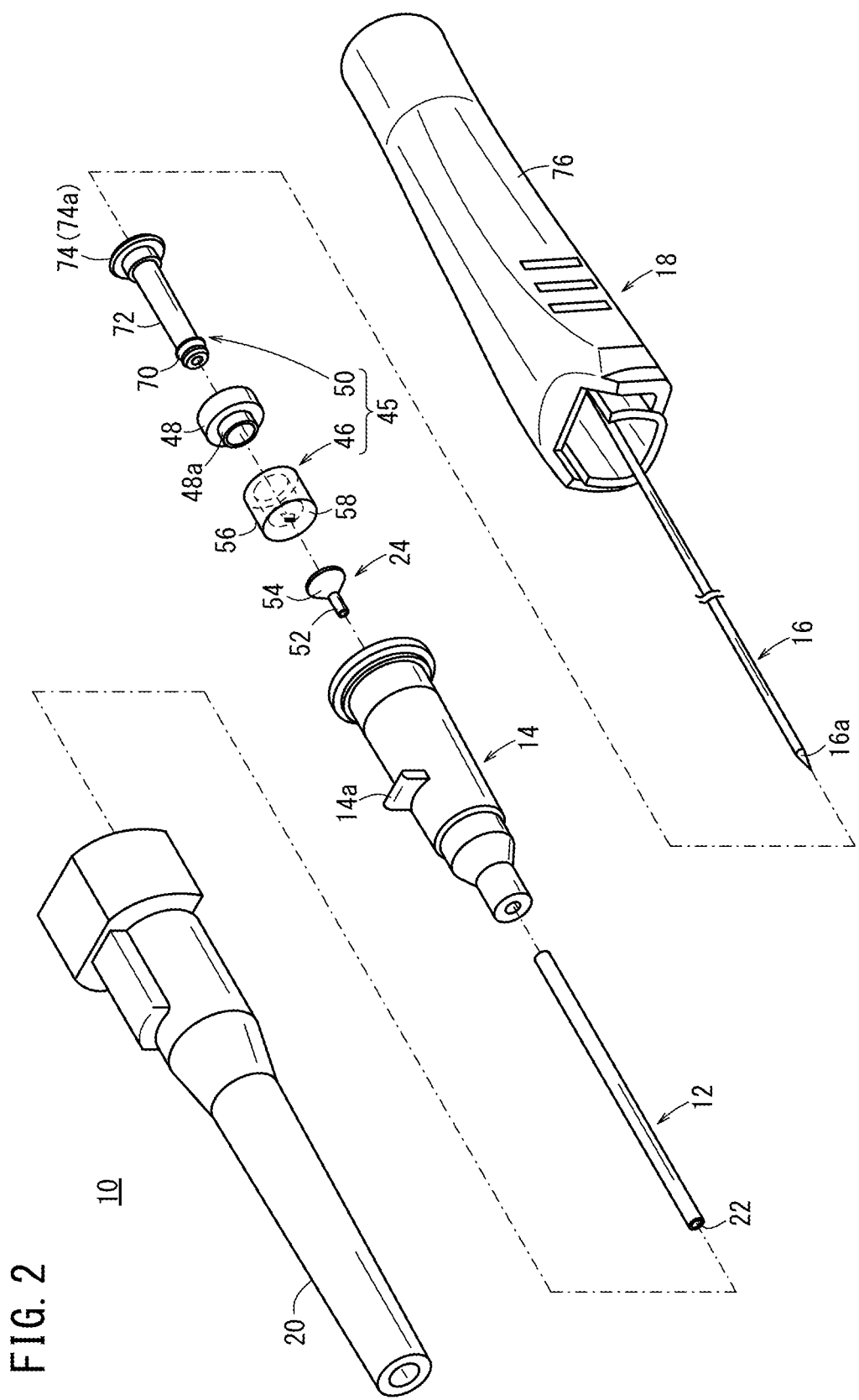
FIG. 2 is an exploded perspective view of the catheter assembly in FIG. 1.
Figure 3:
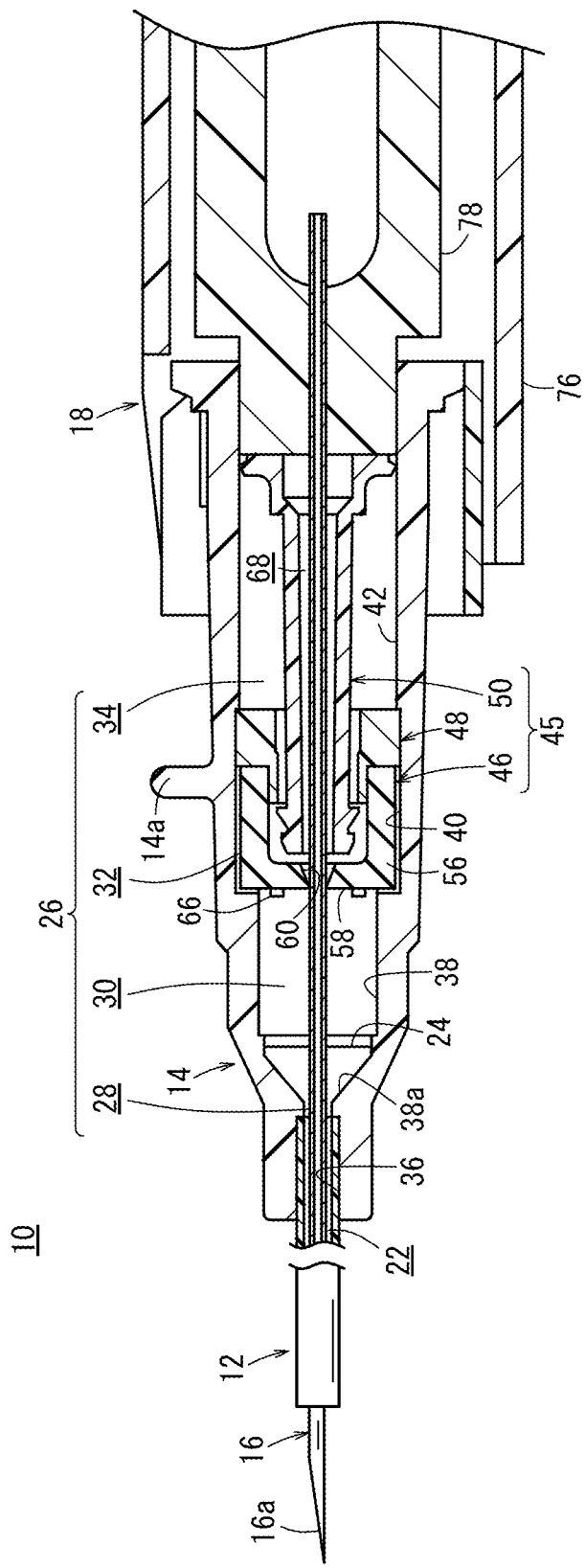
FIG. 3 is a side cross sectional view of the catheter assembly in FIG. 1.

FIG. 1 is an overall perspective view illustrating a catheter assembly 10 according to the embodiment. FIG. 2 is an exploded perspective view of the catheter assembly 10 in FIG. 1. FIG. 3 is a side cross sectional view of the catheter assembly 10 in FIG. 1. Note that, in the description below, the left side in the drawing will be referred to as a distal end (forward) and the right side in the drawing will be referred to as a proximal end (rearward), based on the illustration of the catheter assembly 10 in FIG. 1.

The catheter assembly 10 according to one embodiment includes a tubular catheter 12 (insertion portion), a catheter hub 14 (support portion) connected to the proximal end portion of the catheter 12, a needle 16 having a sharp needle tip 16a on the distal end, and a needle hub 18 connected to the proximal end portion of the needle 16. The catheter assembly 10 pierces a vein (blood vessel) of a patient with the catheter 12 attached together with the needle 16 (the catheter 12 covering the periphery of the needle 16), and then the needle 16 is evulsed together with the needle hub 18. In this manner, the proximal end side of the catheter 12 and the catheter hub 14 are exposed and dwell on the skin of the patient with the distal end side of the catheter 12 inserted in the vein. Then, by connecting a transfusion tube, not illustrated in the drawing, to the proximal end side of the catheter hub 14, transfusion (liquid medicine) can be supplied to the patient from the transfusion tube. Note that, before using the catheter assembly 10, a protector 20 (see FIG. 2) is attached to prevent accidental piercing with the catheter 12 and the needle 16.

The catheter 12 of the catheter assembly 10 is configured as a flexible tubular (cylindrical) member. As a composing material of the catheter 12, a resin, particularly, a soft resin material is preferable. In this case, for example, a fluororesin such as polytetrafluoroethylene (PTFE), ethylene-tetrafluoroethylene copolymer (ETFE), perfluoroalkoxy fluororesin (PFA), an olefin resin such as polyethylene and polypropylene or a mixture thereof, polyurethane, polyester, polyamide, polyether nylon resin, and a mixture of the olefin resin and ethylene-vinyl acetate copolymer may be used.

Further, the catheter 12 may preferably be composed of a transparent resin so that the whole, or a portion of, the inside of the catheter 12 can be seen. For this, when the catheter 12 is inserted and dwelled in the vein, the blood flowing into the catheter hub 14 through a lumen 22 (see FIG. 3) of the catheter 12 (also named as "flashback") can visually be checked.

Further, by mixing an X-ray contrast medium, for example, barium sulfate, barium carbonate, bismuth carbonate, tungstic acid into the composing material of the catheter 12, an imaging function can be provided.

As illustrated in FIG. 2, the proximal end portion of the catheter 12 is fluid-tightly fixed to the distal end portion of the catheter hub 14 by a method, for example, crimping, fusion (heat-fusion, high-frequency fusion, or the like), and adhesion with an adhesive. In the catheter assembly 10 according to the embodiment, the catheter 12 is fixed to and supported by the catheter hub 14 using a crimp pin 24 (also see FIG. 3 and FIG. 4).

As illustrated in FIG. 1 to FIG. 3, the catheter hub 14 is formed with a resin material harder than the catheter 12 and is formed in a cylindrical shape which becomes thinner toward the distal end. The catheter hub 14 fixes and supports the proximal end portion of the catheter 12 so as to make the operation (piercing) of the catheter 12 easy and to allow the catheter 12 to easily communicate with the transfusion tube. Note that, the catheter hub 14 includes a tab 14a which protrudes outward and is provided on the outer circumferential surface of the middle portion in the axial direction. With the tab 14a, the manual advancing (piercing) of the catheter 12 in the vein can easily be carried out.

Further, the lumen of the catheter hub 14 functions as a flow passage 26 which allows the transfusion to flow therein. The flow passage 26 opens at the proximal end surface of the catheter hub 14 and is connected to (communicates with) the lumen 22 of the catheter 12 which is fixed to the distal end portion of the catheter hub 14. Specifically, the flow passage 26 of the catheter hub 14 includes an catheter connection part 28, a distal end guiding part 30, a valve body arrangement part 32, and a connector connection part 34 in this order from the distal end side to the proximal end side (see FIG. 3).

The catheter connection part 28 includes a wall portion 36 (inner diameter) which is approximately identical to the outer diameter of the catheter 12 at the distal end portion of the catheter hub 14. The proximal end portion of the catheter 12 is inserted in the catheter connection part 28.

Further, the distal end guiding part 30 is continuously connected, at the distal end side thereof, to the catheter connection part 28, and thereby functions to guide the transfusion supplied from the proximal end side to the catheter 12. The wall portion 38 constituting the distal end guiding part 30 has a tapered surface 38a of which inner diameter close to the distal end gradually increases toward the proximal end. From the middle portion which is continuously connected to the tapered surface 38a to the proximal end, the wall portion 38 is formed in an approximately parallel shape.

The valve body arrangement part 32 is continuously connected, at the distal end side thereof, to the distal end guiding part 30 and is configured with a wall portion 40 having a larger diameter than that of the wall portion 38 of the distal end guiding part 30. Therefore, a stepped portion is formed between the distal end guiding part 30 and the valve body arrangement part 32. A hemostasis valve 46 and a sealing member 48 which will be described below are arranged in the valve body arrangement part 32.

The connector connection part 34 is continuously connected, at the distal end side thereof, to the valve body arrangement part 32 and extends toward the proximal end. The connector connection part 34 allows a connector 44 (see FIG. 6 and FIG. 7) of the transfusion tube to engage therein. Note that, in FIG. 3, the wall portion 42 constituting the connector connection part 34 is formed in a shape parallel to the axial direction. However, the wall portion 42 of the connector connection part 34 may have a tapered shape in which the inner diameter of the wall portion 42 gradually increases toward the proximal end. With such manner, by forming the distal end portion of the connector 44 in a corresponding tapered shape (tapered angle), the distal end portion of the connector 44 can easily be inserted in the proximal end side of the connector connection part 34 so as to be connected. With the connection made in such manner, the tightness of contact between the wall portion 42 of the connector connection part 34 and the outer circumferential surface of the connector 44 increases, providing connection having higher fluid-tightness.

Figure 4:
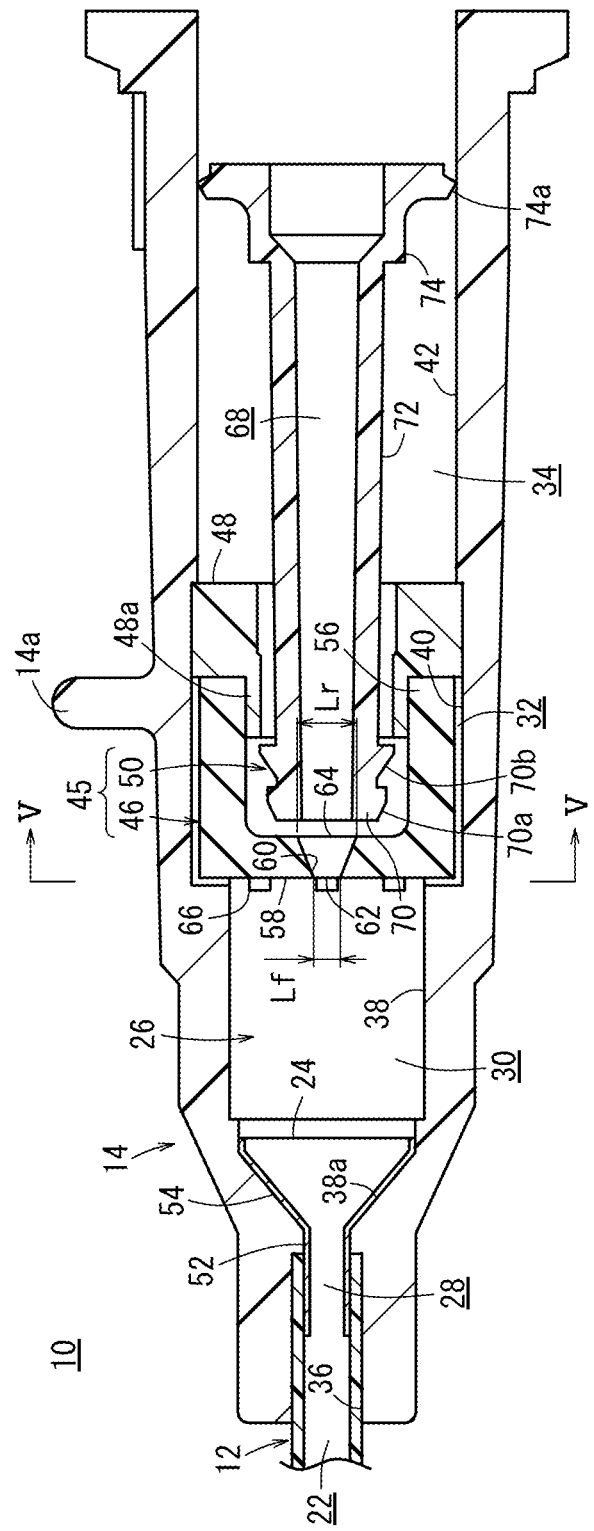
FIG. 4 is a partial side cross sectional view illustrating a state in which a needle and a needle hub are pulled out from the catheter assembly in FIG. 3.
Figure 5:
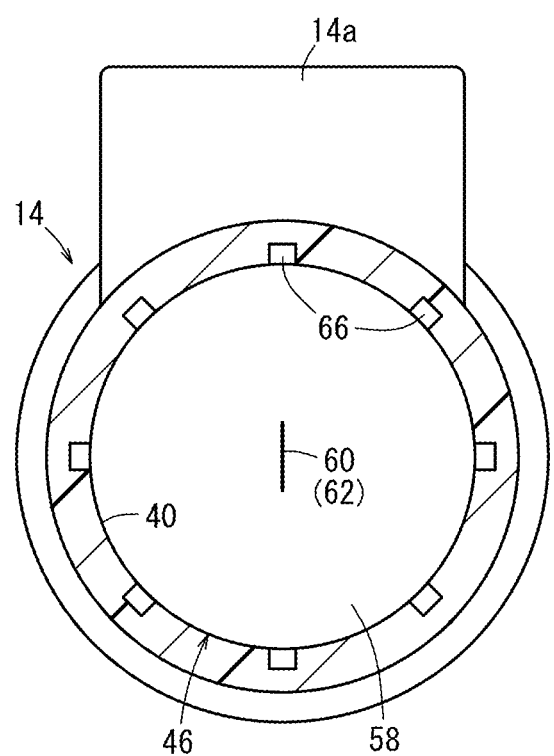
FIG. 5 is a cross sectional view taken along the line V-V in FIG. 4.

FIG. 4 is a partial side cross sectional view illustrating a state in which an needle 16 and an needle hub 18 is pulled out from the catheter assembly 10 in FIG. 3. FIG. 5 is a cross sectional view taken along the line V-V in FIG. 4.

As illustrated in FIG. 2 to FIG. 4, in the flow passage 26 of the catheter hub 14, a crimp pin 24, a hemostasis valve 46 (valve body), a sealing member 48, and a plug 50 (insertion member) are contained in this order from the distal end side. Among these components, the hemostasis valve 46 and the plug 50 function as a valve mechanism 45 which can stop the blood and supply the transfusion to the catheter assembly 10.

As described above, the crimp pin 24 is a member for connecting and fixing the catheter 12 and the catheter hub 14. The crimp pin 24 includes a tubular cylindrical portion 52 in the distal end side and a tapered portion 54 of which diameter gradually increases from the cylindrical portion 52 toward the proximal end side. The cylindrical portion 52 of the crimp pin 24 is contained in the catheter connection part 28 of the catheter hub 14 (flow passage 26), and the tapered portion 54 of the crimp pin 24 is contained in the distal end side of the distal end guiding part 30 of the catheter hub 14.

The cylindrical portion 52 is formed so as that the outer diameter is approximately identical to the lumen 22 of the catheter 12, and extends in the axial direction by a predetermined length. In the catheter assembly 10, the cylindrical portion 52 is inserted and crimps the catheter 12 in the catheter connection part 28 of the catheter hub 14. In this manner, the wall portion 36 of the catheter connection part 28 and the cylindrical portion 52 of the crimp pin 24 surroundingly holds the catheter 12 such that the catheter 12 is fixingly held in the catheter hub 14. Note that, the crimp pin 24 may preferably be formed with a metal or a hard resin to crimp the catheter 12 and the catheter hub 14 with the cylindrical portion 52.

Further, the tapered portion 54 of the crimp pin 24 is formed so as that the outer diameter gradually increases from the distal end side toward the proximal end side, corresponding to the tapered surface 38a of the distal end guiding part 30 of the catheter hub 14. Therefore, the crimp pin 24 is contained in the flow passage 26 with the tapered portion 54 and the tapered surface 38a in a tight contact. When transfusion flows in from the proximal end side, the tapered portion 54 allows the transfusion to smoothly flow out toward the catheter 12.

Note that, when the catheter 12 and the catheter hub 14 are fixed by fusion or an adhesive, the crimp pin 24 is not necessary. In this case, since the distal end guiding part 30 of the catheter hub 14 formed in the tapered surface 38a, when transfusion flows in from the proximal end side, the transfusion smoothly flows out toward the catheter 12.

The hemostasis valve 46 is a member arranged so as to block the flow passage 26 of the catheter hub 14 and has a function of blocking the outflow of the fluid (blood). Specifically, the hemostasis valve 46 is formed in a bottomed cylindrical shape and arranged so as that a side circumferential wall 56 is in tight contact with the wall portion 40 of the valve body arrangement part 32 of the catheter hub 14. Further, the bottom portion of the hemostasis valve 46 is configured as a blocking membrane 58 which blocks the flow of the transfusion. A slit 60 (opening/closing part) is formed in the middle portion of the blocking membrane 58 so as to penetrate the blocking membrane 58.

The blocking membrane 58 has a predetermined membrane thickness and functions as a valve receiving blood flowing into the flow passage 26. That is, the blocking membrane 58 is configured to have predetermined flexibility so as that the slit 60 will not open easily and let the blood flow into the proximal end side of the hemostasis valve 46.

The slit 60 according to one embodiment is formed so as to penetrate the blocking membrane 58 as a single line, in a front view, and to exist as a single plane shape. The slit 60 is configured so that the needle 16 and the plug 50 can be inserted and removed therethrough. The slit 60 is formed to close by itself when the needle 16 and the plug 50 is not inserted.

Further, the slit 60 is formed in an isosceles trapezoid shape in which openings on both sides of the blocking membrane 58 (the distal end opening 62 and the proximal end opening 64) are the bases (the upper base and the lower base) when viewed from a side surface cross sectional view (see FIG. 4). The slit 60 has a relation of $L_f < L_r$, where $L_f$ is a linear length of the distal end opening 62 and $L_r$ is a linear length of the proximal end opening 64. That is, the slit 60 has a shape in which the distance between the legs of the trapezoid shape gradually increases from the distal end opening 62 toward the proximal end opening 64. The specific configuration and effect of the slit 60 will be described in detail below.

The hemostasis valve 46 is preferably composed of a flexible material having a hardness which prevents the slit 60 from opening easily by a blood flow (blood pressure). By composing the hemostasis valve 46 with a flexible material, the plug 50 can easily be inserted through the slit 60. As a flexible material composing the hemostasis valve 46, for example, a rubber material (particularly, a vulcanized rubber material) such as natural rubber, isoprene rubber, butyl rubber, butadiene rubber, styrene-butadiene rubber, urethane rubber, nitrile rubber, acrylic rubber, fluororubber, and silicone rubber, a thermoplastic elastomer such as urethane-based, polyester-based, polyamide-based, olefin-based, and styrene-based, or a mixture thereof may be used. Among these flexible materials, particularly, isoprene rubber is preferably used. When isoprene rubber is used as a composing material of the valve body, there is such advantage that the permanent compression strain is small and the usable years of the product is long.

As illustrated in FIG. 3 to FIG. 5, in the wall portion 40 of the valve body arrangement part 32 in which the hemostasis valve 46 is arranged, a plurality of inner circumferential grooves 66 are provided, the grooves providing communication between the distal end guiding part 30 of the catheter hub 14 and the proximal end side of the valve body arrangement part 32. The inner circumferential groove 66 is formed so as that the distal end portion of the inner circumferential groove 66 cuts into the stepped portion between the distal end guiding part 30 and the valve body arrangement part 32. The inner circumferential groove 66 extends in the axial direction from the distal end portion along the wall portion 40 of the valve body arrangement part 32.

The inner circumferential groove 66 is provided to prevent gas (air) from remaining in the distal end guiding part 30 of the catheter hub 14 after piercing the catheter 12 and the needle 16 into the vein of the patient followed by evulsion of the needle 16. That is, the gas existing closer to the distal end than the hemostasis valve 46 is introduced to the proximal end side, after the needle 16 is evulsed, pushed by the blood flowing into the flow passage 26, thereby passing through the inner circumferential groove 66. Note that, the inner circumferential groove 66 is formed on the wall portion 40 of the catheter hub 14 from the distal end side to the proximal end side not only in a linear shape. The inner circumferential groove 66 may be formed in, for example, a wave-shape or a spiral-shape. Further, the depth of the inner circumferential groove 66 depends on the shape of the catheter hub 14 and the hemostasis valve 46. However, it is preferable to provide a depth of, for example, about 5 to 20 μm. Further, the inner circumferential groove 66 may be formed not only on the wall portion 40 (inner circumferential surface) of the catheter hub 14 but on the side circumferential wall 56 of the hemostasis valve 46.

Further, the catheter assembly 10 according to the embodiment is provided with the sealing member 48 in the proximal end side of the hemostasis valve 46 so as to block the inner circumferential groove 66. The sealing member 48 is formed in a cylindrical shape and has sealability allowing gas to permeate but fluid not to permeate. The sealing member 48 is arranged so as to contact tightly with the hemostasis valve 46 and to block the inner circumferential groove 66. In order to enhance the tight-contact with the hemostasis valve 46, the distal end portion of the sealing member 48 is formed in a cylindrical protruding portion 48a which engages in the proximal end side opening of the hemostasis valve 46. Further, the sealing member 48 can be fixed to the wall portion 40 of the catheter hub 14 (valve body arrangement part 32) by a method such as fusion or adhesion. The displacement of the distal end side and the proximal end side of the hemostasis valve 46 and the sealing member 48 are restricted by the valve body arrangement part 32 of the catheter hub 14. Therefore, even when the needle 16 or the plug 50 is removed, the arranged location of the hemostasis valve 46 is maintained, thereby providing smooth opening/closing operation of the slit 60.

A sealing member 48 that is gas permeable but inhibits permeation of fluid is used. As such sealing member 48, a sealing member formed with, for example, a porous material such as a sintered material made of polyethylene can preferably be used. A sealing member 48 of a porous material is also preferable in that it is easy to produce and can be produced with high accuracy.

Further, the plug 50 which constitutes the valve mechanism 45 together with the hemostasis valve 46 is formed in an approximately cylindrical shape with a hard resin material. The plug 50 is arranged closer to the proximal end than the blocking membrane 58 in the flow passage 26 of the catheter hub 14 and configured to advance freely in the axial direction of the catheter hub 14. The lumen 68 of the plug 50 functions as a flow passage which allows transfusion to pass therethrough. The plug 50 advances toward the distal end of the catheter hub 14 by a predetermined operation (pushing operation of the connector 44 made when the transfusion tube is connected) and is inserted in the slit 60 of the hemostasis valve 46, thereby providing communication between the distal end guiding part 30 (flow passage 26) of the catheter hub 14 and the lumen 68.

The plug 50 is formed to have a distal end expanding portion 70, a body portion 72, and a proximal end expanding portion 74, from the distal end side, in this order. The distal end expanding portion 70 is a member which penetrates the hemostasis valve 46 (slit 60) and is arranged in the distal end guiding part 30 of the catheter hub 14, along with the advancement of the plug 50. On the outer circumferential surface of the distal end expanding portion 70, two brims (a first brim 70a and a second brim 70b) protruding outward along the radial direction and extending along the circumferential direction are arrayed in the axial direction.

The second brim 70b functions as an engagement portion which engages with the slit 60 of the hemostasis valve 46 with the plug 50 penetrating (inserted in) the slit 60. That is, by the second brim 70b of the plug 50 engaging with the slit 60 of the hemostasis valve 46, unintentional movement of the plug 50 toward the proximal end is prevented, so that the flow passage 26 of the catheter hub 14 is surely kept in communication with the lumen 68 of the plug 50.

These first and second brims 70a and 70b are formed in a tapered shape in which the diameter gradually increases from the distal end toward the proximal end. Being formed in the tapered shape as described above, when the plug 50 penetrates the slit 60 of the hemostasis valve 46, the first brim 70a and the second brim 70b surely press the slit 60 outward one after another, allowing the penetration easy to be carried out.

The body portion 72 of the plug 50 is continuously connected to the distal end expanding portion 70 and extends toward the proximal end at a predetermined length. When the plug 50 is contained in the flow passage 26 of the catheter hub 14, the body portion 72 is arranged through the valve body arrangement part 32 and the connector connection part 34.

The proximal end expanding portion 74 is continuously connected to the proximal end side of the body portion 72 so that the proximal end expanding portion 74 is arranged in the connector connection part 34 of the catheter hub 14. On the outer circumferential surface, close to the proximal end, of the proximal end expanding portion 74, a flange 74a extending outward along the radial direction and extending along the circumferential direction is formed. The flange 74a is formed to have an outer diameter approximately identical to the wall portion 42 (inner diameter) of the connector connection part 34 of the catheter hub 14. Therefore, when the plug 50 advances, the flange 74a slides against the wall portion 42 of the connector connection part 34, and thereby the movement is stably carried out.

Before the plug 50 advances, the plug 50 exists closer to the proximal end than the slit 60 so that the slit 60 closes by itself, thereby blocking the flow passage 26. And when the plug 50 advances, the distal end expanding portion 70 penetrates the slit 60 to move toward the distal end side farther than the hemostasis valve 46, thereby connecting the lumen 68 of the plug 50 and the flow passage 26. That is, the catheter assembly 10 provides communication between the flow passage 26 and the lumen 68 of the plug 50 by advancing the plug 50 along the axial direction of the flow passage 26 so as to insert the distal end expanding portion 70 in the slit 60 of the hemostasis valve 46 (see FIG. 7).

Referring back to FIG. 3, the proximal end portion of the needle 16 of the catheter assembly 10 is fixed to the needle hub 18, and is formed to have a length allowing the needle 16 to penetrate the catheter 12 and the catheter hub 14 from the proximal end portion toward the distal end portion. When the catheter assembly 10 is assembled, the needle 16 is inserted through the catheter 12, the catheter hub 14, the hemostasis valve 46, and the plug 50. In this manner, a sharp needle tip 16a of the needle 16 is configured to protrude from the distal end opening of the catheter 12, thereby allowing the needle tip 16a to easily pierce the surface of a living body. As for a material composing the needle 16, a metal material, for example, a stainless steel, aluminum or an aluminum alloy, or titanium or a titanium alloy may be used.

Note that, on the outer circumferential portion of the needle 16, a groove not illustrated in the drawing may be provided along the axial direction of the needle 16. The groove can function as an introducing passage which introduces blood to the lumen 22 of the catheter 12 when the catheter 12 and the needle 16 are pierced in a blood vessel. The blood introduced to the groove flows into a space between the catheter 12 and the needle 16. In this manner, a flashback of the blood can surely be checked at an earlier timing.

The needle hub 18 includes a case 76 by which the needle 16 can be operated from the proximal end side. Inside the case 76, a fixing block 78 which fixes and holds the needle 16 is provided. The case 76 is formed in a thin long shape which is easy to grip by a hand. Further, the needle hub 18 can be connected to the proximal end side of the catheter hub 14. In this manner, the piercing of the catheter 12 and the needle 16 can easily be carried out by operating the needle hub 18.

As described above, with the catheter assembly 10, the catheter 12 and the needle 16 are pierced in the vein of the patient, and then, the operation of pulling out (evulsing) the needle 16 inserted in the catheter 12 is carried out. The user of the catheter assembly 10 can easily remove the needle 16 from the catheter 12 by gripping and pulling the needle hub 18 (case 76) to pull out the needle 16.

As a material composing the catheter hub 14 and the needle hub 18, a resin material, for example, polyolefin such as polyethylene, polypropylene, and ethylene-vinyl acetate copolymer, polyurethane, polyamide, polyester, polycarbonate, polybutadiene, polyvinyl chloride may be used. Further, by composing the plug 50 with the same material, production cost can be reduced.

Figure 6:
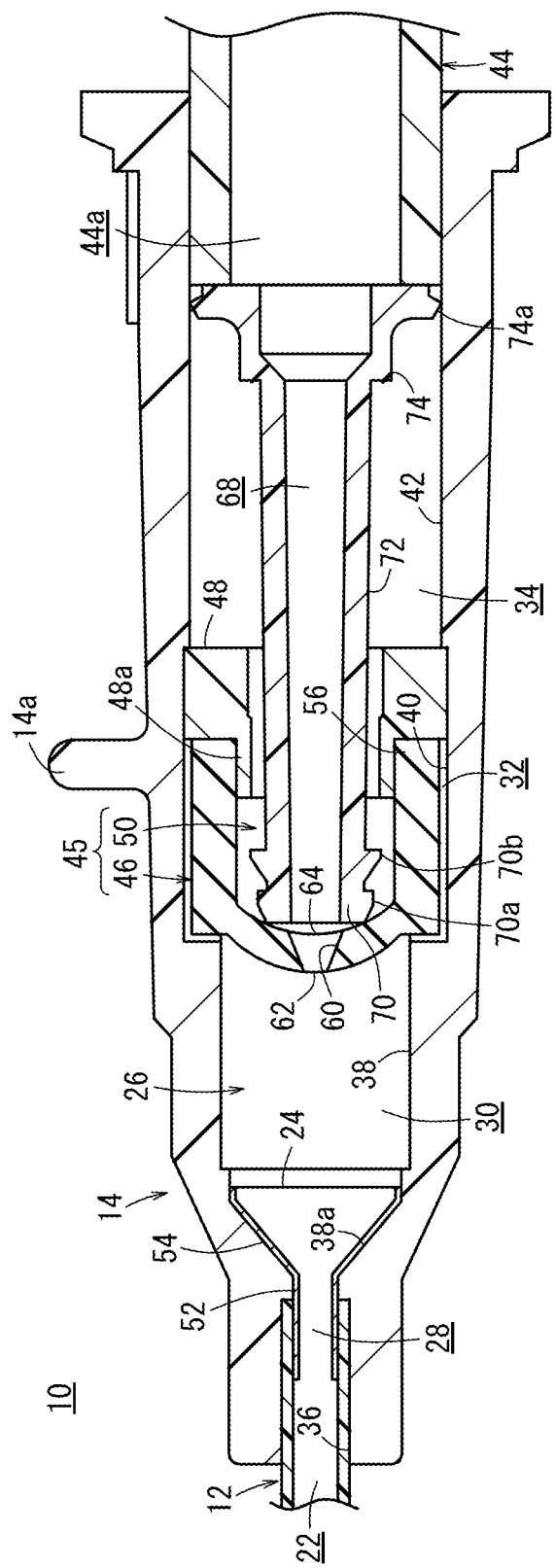
FIG. 6 is a partial side cross sectional view illustrating a state in which a plug is partially advanced in the catheter assembly in FIG. 4.
Figure 7:
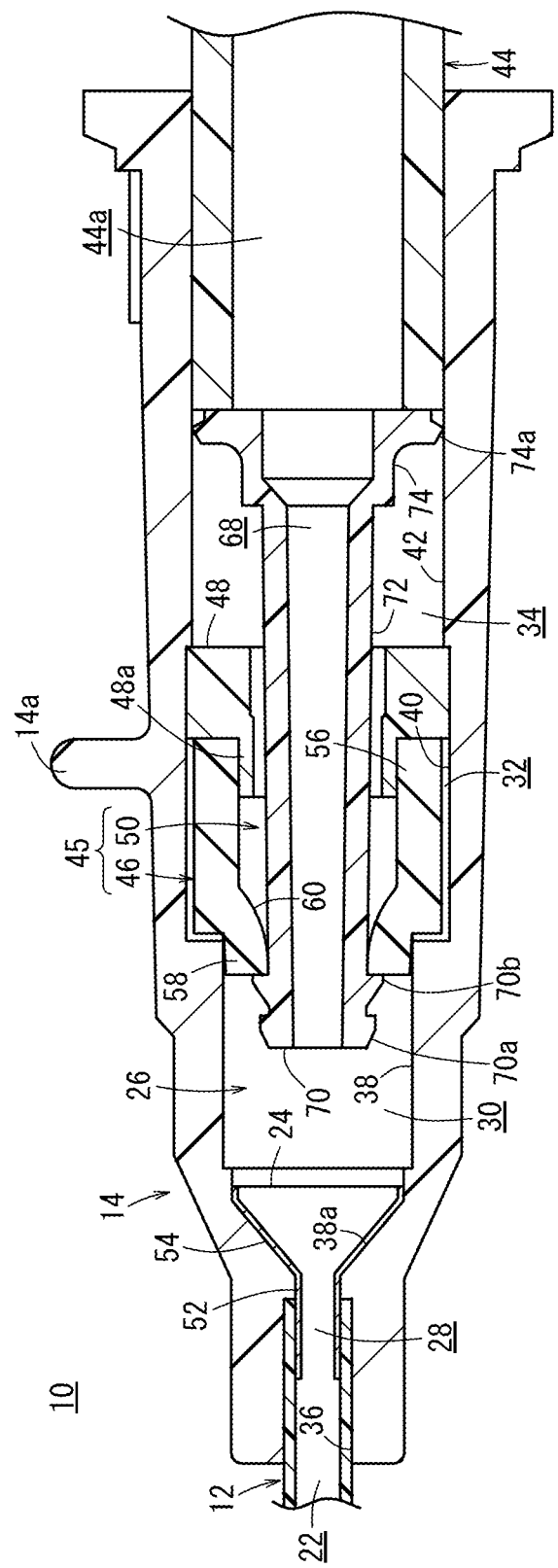
FIG. 7 is a partial side cross sectional view illustrating a state in which a plug is advanced so as to be inserted in a hemostasis valve in the catheter assembly in FIG. 6.

FIG. 6 is a partial side cross sectional view illustrating a state in which a plug 50 is partially advanced in the catheter assembly 10 in FIG. 4. FIG. 7 is a partial side cross sectional view illustrating a state in which a plug 50 is advanced so as to be inserted in a hemostasis valve 46 in the catheter assembly 10 in FIG. 6.

As illustrated in FIG. 6 and FIG. 7, in the catheter assembly 10, the cylindrical connector 44 is inserted in the connector connection part 34 of the catheter hub 14 after evulsing the needle 16. The connector 44 is formed to have an outer diameter approximately identical to the wall portion 42 (inner diameter) of the connector connection part 34. By inserting the connector 44 in the connector connection part 34, the connector 44 engages with the catheter hub 14 so as to maintain the connected state. When the connector 44 is connected to the catheter hub 14, the distal end surface of the connector 44 makes contact with the proximal end expanding portion 74 of the plug 50, thereby providing communication between the lumen 68 of the plug 50 and the lumen 44a of the connector 44.

Further, to the proximal end portion of the connector 44, the distal end portion of the transfusion tube, not illustrated in the drawing, is previously connected. And to the proximal end portion of the transfusion tube, a transfusion bag, not illustrated in the drawing, filled with transfusion fluid is connected. Therefore, the catheter assembly 10 is supplied with transfusion fluid via the transfusion bag, the transfusion tube, and the connector 44, and can further introduce the transfusion fluid to the flow passage 26 of the catheter hub 14 and the lumen 22 of the catheter 12 through the lumen 68 of the plug 50.

Note that, to surely supply the transfusion fluid, a locking mechanism (not illustrated in the drawing) which keeps a connected state may preferably be provided to the catheter hub 14 and the connector 44. Further, the distal end portion of the connector 44 may be formed in a tapered shape in which the outer diameter of the distal end portion gradually increases toward the proximal end. In this manner, when connecting the connector 44, the connector 44 can easily be inserted in the proximal end side of the catheter hub 14, and can easily be removed from the catheter hub 14 after supplying transfusion.

Further, the plug 50 may be configured to have the inner diameter of the proximal end expanding portion 74 same as, or larger than, the inner diameter of the connector 44. In this manner, when the connector 44 is connected to the proximal end portion of the catheter hub 14, the inflow of transfusion from the connector 44 into the plug 50 can easily and surely be provided.

The catheter assembly 10 according to the embodiment is basically configured as described above. Now, the operation and effect, when the catheter assembly 10 is used, will be described.

The catheter assembly 10 is provided, before used, with each of the components illustrated in FIG. 2 assembled. That is, as illustrated in FIG. 3, the proximal end portion of the catheter 12 is fixed to the catheter hub 14 and the catheter 12 protrudes toward the distal end. Each of the crimp pin 24, the hemostasis valve 46, the sealing member 48, and the plug 50 is arranged at each predetermined location in the inside (flow passage 26) of the catheter hub 14. Further, the proximal end portion of the needle 16 is fixed to the needle hub 18. The needle 16 is inserted through the catheter hub 14 and then through the lumen 22 of the catheter 12. The needle tip 16a of the needle 16 exposes itself from the distal end portion of the catheter 12. In the flow passage 26 of the catheter hub 14, the needle 16 penetrates the slit 60 of the hemostasis valve 46 and the lumen 68 of the plug 50 to be connected to the needle hub 18. Further, the protector 20 (see FIG. 2) is attached to the catheter assembly 10 so as to cover, from the distal end of the catheter hub 14, the catheter 12 and the needle 16.

Therefore, when using the catheter assembly 10 the protector 20 is first removed, and then, the catheter assembly 10 is positioned at a desired location (location in which piercing is carried out) on the patient. Then, the needle hub 18 is gripped to pierce the needle 16 and the catheter 12 into the vein of the patient. When the catheter 12 and the needle 16 are inserted in the vein, the blood flows through the space between the catheter 12 and the needle 16 toward the proximal end by the blood pressure. At this time, since the catheter 12 or the catheter hub 14 are formed with a transparent material, the inflow of the blood can be seen.

The blood flowing into the catheter hub 14 reaches the distal end guiding part 30 of the flow passage 26, and blocked by the hemostasis valve 46 to flow out further in the proximal end side. During this inflow of the blood, the air existing in the distal end guiding part 30 passes through the inner circumferential groove 66 and is exhausted to the proximal end side of the catheter hub 14 via the sealing member 48 which allows gas to permeate therethrough.

After the inflow of the blood is seen, the catheter assembly 10 is further advanced toward the distal end by a slight distance. Specifically, by putting a finger on the tab 14a of the catheter hub 14, the catheter 12 and the needle 16 are advanced by a predetermined distance relative to the vein. After advancing the catheter 12, by fixing the catheter 12 or the catheter hub 14 with a hand, gripping the needle hub 18 with another hand, and pulling the needle hub 18 toward the proximal end, the needle 16 is evulsed from the catheter 12. In this manner, the catheter assembly 10 is in a state in which the catheter 12 and the catheter hub 14 dwells in the patient. Note that, the evulsed needle 16 is no longer necessary and is disposed.

As illustrated in FIG. 4 and FIG. 5, in the catheter assembly 10, the slit 60 of the hemostasis valve 46 is closed when the needle 16 has been evulsed, so that the blood flowing into the flow passage 26 (distal end guiding part 30) is prevented from flowing outside (leaking) from the proximal end side of the catheter hub 14.

As described above, the hemostasis valve 46 according to one embodiment has the linear length $L_f$ of the distal end opening 62 of the slit 60 (opening/closing part) formed in a single line shorter than the linear length $L_r$ of the proximal end opening 64. Therefore, even when pressing force (blood pressure) is applied from the blood flowing into the flow passage 26 of the catheter hub 14, the blood is prevented from flowing out at the distal end opening 62 having shorter linear length $L_f$. That is, the hemostasis valve 46 can surely stop (block) the blood by the blocking membrane 58.

Note that, the linear length $L_f$ at the distal end opening 62 of the slit 60 depends on the size of the hemostasis valve 46 and the membrane thickness of the blocking membrane 58. However, for example, it is preferable to provide the linear length $L_f$ within a range of 0.3 to 0.6 mm. By providing the linear length $L_f$ within a range of 0.3 to 0.6 mm, sufficient hemostasis of blood can be obtained so that the outflow of blood can surely be prevented. Further, corresponding to the linear length $L_f$ at the distal end opening 62, the linear length $L_r$ at the proximal end opening 64 of the slit 60 may preferably be provided within a range of 0.4 to 0.8 mm. That is, the linear length $L_r$ at the proximal end opening 64 may preferably be provided longer than the linear length $L_f$ at the distal end opening 62 by about 30% regarding relation of insertion property of the plug 50.

After the needle 16 is evulsed, the catheter hub 14 is fixed on the skin of the patient by an adhesive tape or the like. As illustrated in FIG. 6, the connector 44 of the transfusion tube is inserted from the proximal end side of the catheter hub 14. By insertion of the connector 44, the plug 50 contained in the flow passage 26 of the catheter hub 14 moves toward the distal end pressed by the connector 44, and the distal end expanding portion 70 of the plug 50 pushes itself into the blocking membrane 58 of the hemostasis valve 46.

Thereby, as illustrated in FIG. 7, the distal end portion of the plug 50 is inserted in the slit 60 of the blocking membrane 58. In this case, the hemostasis valve 46 according to the embodiment has the long linear length $L_r$ at the proximal end opening 64 of the slit 60 so that the plug 50 can be easily inserted in the slit 60. That is, when the distal end surface of the plug 50 (distal end expanding portion 70) presses, by making contact with, the proximal end surface of the blocking membrane 58 of the hemostasis valve 46, the blocking membrane 58 elastically deforms and the center portion of the blocking membrane 58 is displaced toward the distal end. The deformation of the blocking membrane 58 expands the proximal end opening 64, so that the distal end expanding portion 70 can easily enter into the slit 60.

Consequently, the plug 50 can be inserted through the slit 60 at a stage in which the pushed-in distance of the plug 50 (the volume of deformation of the blocking membrane 58) is small, thereby reducing the pressing force (insertion force) applied on the connection of the transfusion tube. As a result, the connecting operation of the transfusion tube can be carried out in a short time, further allowing the plug 50 to surely penetrate the hemostasis valve 46. Further, the load applied on the hemostasis valve 46 which is being elastically deformed is reduced.

As described above, the valve mechanism 45 improves penetrability during the insertion of the plug 50, and by the plug 50 being smoothly inserted in the hemostasis valve 46, the blood can be prevented from flowing out to the proximal end side of the blocking membrane 58. That is, the catheter assembly 10 also improves hemostasis during insertion of the plug 50.

When the plug 50 is inserted until the second brim 70b reaches the distal end opening 62 of the hemostasis valve 46, the second brim 70b is hooked on the rim of the slit 60, thereby preventing the plug 50 from coming off. In this manner, the communication between the flow passage 26 (distal end guiding part 30) of the catheter hub 14 and the lumen 68 of the plug 50 is provided, thereby allowing the transfusion to be introduced from the transfusion tube to the catheter 12.

Then, the supplying of transfusion fluid from the transfusion bag starts. The transfusion fluid which passes through the transfusion tube and then the connector 44 flows out from the opening of the distal end expanding portion 70 of the plug 50 to be filled in the entire flow passage 26. Further, the transfusion fluid is introduced in the vein of the patient via the flow passage 26 of the catheter hub 14 through the lumen 22 of the catheter 12.

As described above, according to the catheter assembly 10 according to the embodiment, the slit 60 of the hemostasis valve 46 is formed in a single slit shape penetrating the blocking membrane 58, and is formed to have the relation of $L_f < L_r$, where $L_f$ is a linear length at the distal end opening 62 from which the plug 50 protrudes and $L_r$ is a linear length at the proximal end opening 64 in which the plug 50 is inserted. So that when the plug 50 is not inserted in the slit 60, the slit 60 can surely be closed since the linear length $L_f$ at the distal end opening 62 is short, thereby preventing blood from flowing out to the proximal end side of the catheter hub 14. Further, when the plug 50 is inserted in the slit 60, the plug 50 can easily enter into the proximal end opening 64 since the linear length $L_r$ at the proximal end opening 64 is long. That is, as for the catheter assembly 10, the hemostasis of blood and the penetrability of the plug 50 are simultaneously improved so that the outflow of blood of the patient is drastically reduced and the efficiency of connecting operation of the transfusion tube is further improved.

Further, in the catheter assembly 10 according to one embodiment, the slit 60 is formed in an isosceles trapezoid shape in which the distal end opening 62 and the proximal end opening 64 are the upper base and the lower base of the isosceles trapezoid shape, respectively, when viewed in a side cross sectional view of the hemostasis valve 46. In this manner, when the plug 50 is inserted from the proximal end side of the hemostasis valve 46, the plug 50 inserted from the proximal end opening 64 of the slit 60 is squeezed by uniform contacting force from both legs of the trapezoid shape and can advance smoothly toward the distal end opening 62 of the slit 60, thereby further improving the penetrability of the plug 50.

Note that, the catheter assembly 10 according to the present invention is not limited to the embodiment described above. It goes without saying that various configurations may be employed without departing from the spirit and the scope of the invention.

EXAMPLE

Comparison is made regarding penetrability and hemostasis for the hemostasis valve 46 including the slit 60 according to an embodiment of the present invention and a hemostasis valve including a silt having another shape. Note that a catheter assembly 10 having the same components, except the hemostasis valve, is used in the comparison.

FIG. 8 is a table in which penetrability and hemostasis for a slit 60 of the hemostasis valve 46 according to one embodiment (example) and for a slit of a hemostasis valve of comparative examples 1 to 4 are shown.

As illustrated in FIG. 8, for the hemostasis valve 46 of the inventive example, the linear length $L_f$ at the distal end opening 62 is provided to be 0.3 mm, and the linear length $L_r$ at the proximal end opening 64 is provided to be 0.4 mm. For the hemostasis valve of the comparative example 1, the linear length $L_f$ at the distal end opening and the linear length $L_r$ at the proximal end opening are provided to be the same value of 0.3 mm. Further, for the hemostasis valve of the comparative example 2, the linear length $L_f$ at the distal end opening and the linear length $L_r$ at the proximal end opening are provided to be the same value of 0.4 mm. Further, for the hemostasis valve 46 of the comparative example 3, the linear length $L_f$ at the distal end opening is provided to be 0.4 mm, and the linear length $L_r$ at the proximal end opening is provided to be 0.3 mm. Furthermore, for the comparative example 4, a front view of the blocking membrane is illustrated. The hemostasis valve according to the comparative example 4 is formed to have a slit extending in three directions, evenly spaced between each other, from the center of the blocking membrane (forming a Y-shape).

Further, the pressure which the slit of the hemostasis valve receives from the fluid is measured as a standard to assess hemostasis. The pressure which is measured when the fluid is actually flowing out is compared. The deformation (distance by which the center portion moves toward the distal end: a stroke of the plug) of the hemostasis valve when the plug is inserted is measured as a standard to assess penetrability. The amount of displacement which is measured when the plug is actually inserted is compared.

The hemostasis valve 46 of the example is able to receive a pressure of about 80 kPa from the fluid. A displacement of about 2.5 mm is measured as the stroke of the plug 50. For comparative example 1, hemostasis of blood is measured to be about the same level as the example, but a displacement of 3.5 mm is measured as the stroke of the plug, resulting in reduction of penetrability of the plug. Further, for the comparative example 2, penetrability of the plug is measured to be about the same level as the example, but a pressure of about 60 kPa is received from the fluid, resulting in reduction of hemostasis. Furthermore, for comparative example 3, similarly to the comparative example 1, hemostasis is measured to be about the same level as the example, but the result shows that the penetrability of the plug decreased. Furthermore, for comparative example 4, a displacement of about 1.5 mm is measured as the stroke of the plug showing superiority in penetrability, but a pressure of about only 8 kPa is received from the fluid, resulting in drastic reduction in hemostasis.

As described above, the result for comparative examples 1 to 4 shows deterioration in either of penetrability and hemostasis. However, the inventive example shows good result for both penetrability and hemostasis.

What is claimed is:

1. A catheter assembly comprising:
a tubular insertion portion;
a support portion that is connected to a proximal end side of the insertion portion and has therein a flow passage communicating with an inside of the insertion portion;
a valve body that is disposed in the flow passage and includes:
a blocking membrane configured to inhibit a flow of fluid, and
an opening/closing part configured such that the blocking membrane is at least partially openable and closeable via the opening/closing part; and
an insertion member which is arranged proximal of the opening/closing part and is insertable into the opening/closing part by moving in a distal direction,
wherein the opening/closing part is formed as a single slit penetrating the blocking membrane, the slit having a distal end opening and a proximal end opening, and a length of the distal end opening being smaller than a length of the proximal end opening when an entirety of the insertion member is located outside of the opening/closing part.

2. The catheter assembly according to claim 1, wherein the opening/closing part is formed in an isosceles trapezoid shape in which the distal end opening and the proximal end opening are an upper base and a lower base of the isosceles trapezoid shape, respectively, when viewed in a side cross sectional view of the valve body.

3. The catheter assembly according to claim 1, further comprising a sealing member disposed proximal of the valve body so as to block the flow passage, the sealing member being permeable to gas, and the sealing member being configured to inhibit permeation of fluid.

4. The catheter assembly according to claim 1, further comprising:
an needle which is disposed in the insertion portion; and
an needle hub which is fixed to a proximal end portion of the needle and is connectable to a proximal end side of the support portion.

5. The catheter assembly according to claim 1, wherein the length of the distal end opening is within a range of 0.3 mm to 0.6 mm, and the length of the proximal end opening is within a range of 0.4 mm to 0.7 mm.

6. The catheter assembly according to claim 1, wherein the length of the proximal end opening is about 30% larger than the length of the distal end opening.

* * * * *